United States Patent [19]
Luther et al.

[11] Patent Number: 6,088,889
[45] Date of Patent: *Jul. 18, 2000

[54] CLAMP OPERABLE AS A HEMOSTASIS VALVE

[75] Inventors: Ronald B. Luther, Newport Beach; Edward E. Elson, Anaheim, both of Calif.

[73] Assignee: Edward Elson, Anaheim, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/922,410

[22] Filed: Sep. 3, 1997

[51] Int. Cl.⁷ ............................. A44B 21/00; A61B 17/00
[52] U.S. Cl. ................... 24/489; 24/546; 24/534; 24/533; 606/158
[58] Field of Search ................ 24/489, 499, 543, 24/545, 546, 517, 587, 542, 570, 567, 564, 67.9, 67.5, DIG. 10, DIG. 29, 533, 534; 606/158, 34, 250

[56] References Cited

U.S. PATENT DOCUMENTS

| | | | |
|---|---|---|---|
| 2,685,679 | 8/1954 | Sam | 24/545 X |
| 3,579,751 | 5/1971 | Jonckheere | 24/564 |
| 3,598,125 | 8/1971 | Cogley | 24/510 X |
| 4,071,930 | 2/1978 | Tanaka | 24/543 |
| 4,079,765 | 3/1978 | Hatayan | 24/545 X |
| 4,681,109 | 7/1987 | Arroyo | 128/335 |
| 4,715,377 | 12/1987 | Arroyo | 128/335 |
| 4,777,950 | 10/1988 | Kees, Jr. | 24/546 X |
| 4,802,263 | 2/1989 | Lorber | 24/67.5 |
| 5,011,487 | 4/1991 | Shichman | 606/158 |
| 5,074,870 | 12/1991 | Von Zeppelin | 606/158 |
| 5,179,768 | 1/1993 | Jio | 24/534 X |
| 5,305,500 | 4/1994 | Tucker | 24/30.5 |
| 5,683,405 | 11/1997 | Yacoubian et al. | 606/158 |

*Primary Examiner*—James R. Brittain
*Assistant Examiner*—Robert J. Sandy
*Attorney, Agent, or Firm*—Stetina Brunda Garred & Brucker

[57] ABSTRACT

A manually operable clip operable as a hemostasis valve for use with intravenously inserted catheters. The valve preferably comprises a unitary piece of wire formed to have first and second jaw portions defining front and back ends that preferably include transversely extending arms formed thereon. The valve is further formed such that a spring portion is provided interconnecting the first and second jaw portions that extends intermediate the front and back ends thereof and between said transversely extending arms which is operable to bias the front ends towards each other such that when positioned upon the catheter, such biasing force causes the lumen thereof to assume a closed state. The back ends of the first and second jaw portions may be manually actuated to release the clip from the catheter.

5 Claims, 1 Drawing Sheet

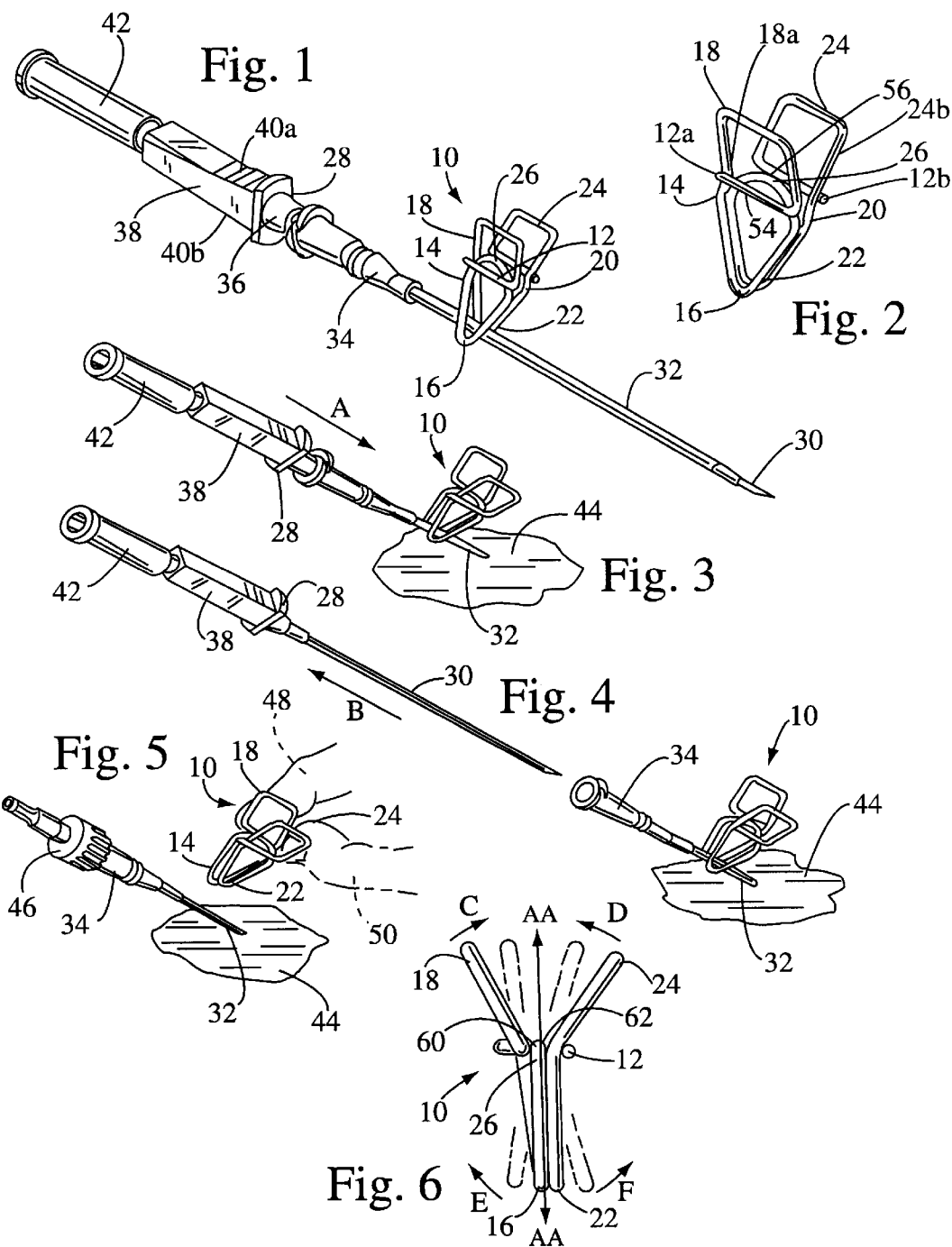

CLAMP OPERABLE AS A HEMOSTASIS VALVE

FIELD OF THE INVENTION

The present invention relates generally to clamping devices, and more particularly, hemostasis valves for use with intravenously inserted catheters.

BACKGROUND OF THE INVENTION

The use of catheters for establishing an intravenous connection into the body is well known in the art. The use of catheters to establish such intravenous connection into the body are taught, for example, in U.S. Pat. No. 4,950,252 to Luther et al., the teachings of which are expressly incorporated herein by reference. In this regard, such catheters provide the primary means by which fluids and drugs may be administered to a patient. Indeed, such catheters, via their intravenous connection, are of vital importance when it becomes necessary to rapidly infuse a given substance into the body, which frequently occurs during surgery and various types of intravenous therapy, such as chemotherapy.

Notwithstanding their immense practicality and widespread use, most catheters currently in use are typically not provided with means for selectively closing off and re-opening the intravenous passageway formed thereby. Specifically, while such catheters effectively allow for fluids, drugs, and the like to pass readily into the bloodstream when a conventional fluid line is connected thereto, once such fluid line is removed there is typically lacking a mechanism for preventing back-flow of blood through the catheter and out of the patient's body. As a result, a new catheter must be utilized to establish an intravenous connection each time it becomes necessary to administer fluids, drugs, etc. intravenously, which thus results in greater patient discomfort, as well as requires that a new catheter be utilized each time it is necessary to establish an intravenous connection into the body.

As such, there is a need in the art for a hemostasis valve that is specifically designed and adapted to be utilized in connection with an intravenously inserted catheter to provide means for forming a re-sealable closure therethrough. There is additionally a need in the art for a hemostasis valve designed to be utilized with an intravenously inserted catheter that is of simple construction, is easy and inexpensive to manufacture, and may be readily and easily utilized with virtually all types of existing catheters. Still further, there is a need in the art for a manually-operable, general utility clamp that in addition to being utilized as a hemostasis valve may be utilized for a variety of routine applications.

SUMMARY OF THE INVENTION

The present invention specifically addresses and alleviates the aforementioned deficiencies in the art. Specifically, the present invention is directed to a hemostasis valve for use with an intravenously inserted catheter that may further be utilized as a general utility clamp for use in a variety of everyday applications. In a preferred embodiment, the valve comprises a unitary piece of wire having opposed ends formed to have first and second jaw portions with each respective jaw portion having a front end and a back end. Each jaw portion is further preferably configured such that an arm formed from a respective opposed end of the wire extends thereacross and intermediate the front and back ends thereof. Extending between and interconnecting the first and second jaw portions and sandwiched between the transverse arms thereof is a spring portion that is operable to normally bias the front ends of the respective jaw portions toward and preferably into abutting contact with each other. The back ends of each respective jaw portion may be selectively compressed toward each other to overcome the biasing force exerted by the spring portion to thus cause the front ends of each jaw portion to separate from each other.

When the front ends are separated, a catheter preferably having an introducer interconnected therewith may be inserted therebetween. The back ends of the valve may then be released, thus allowing the front ends of the jaw members to bias inwardly toward each other and produce a clamping effect thereabout. The catheter may thus be inserted, via the introducer, into the patient with the introducer subsequently being removed therefrom. The catheter will thus remain in the patient with the valve affixed thereto, the latter providing means for forming a hemostatic closure within the catheter which may be selectively removed to thus allow fluids, medicines and the like to be subsequently administered intravenously therethrough. The valve may further be formed to be either disposable or sterilizable. The valve may also be utilized as a general utility clamp for use in a wide variety of applications, such as a paper clip, for example.

It is therefore an object of the present invention to provide a hemostasis valve that prevents the back-flow of blood through an intravenously inserted catheter by forming a resealable closure within the lumen thereof.

Another object of the present invention is to provide a hemostasis valve that selectively permits fluids and medicines to be intravenously administered through an intravenously inserted catheter.

Another object of the present invention is to provide a hemostasis valve that is of simple construction, easy and inexpensive to manufacture, and is simple and easy to use.

A still further object of the present invention is to provide a general utility clamping device that, in addition to functioning as a hemostasis valve, may be utilized for a variety of practical every day applications.

BRIEF DESCRIPTION OF THE DRAWINGS

These, as well as other features of the present invention, will become more apparent upon reference to the drawings, wherein:

FIG. 1 is a perspective view of a catheter axially mounted upon an introducer having a hemostasis valve constructed in accordance with a preferred embodiment of the present invention attached thereto;

FIG. 2 is a perspective view of the hemostasis valve of the present invention;

FIG. 3 is a perspective view of the catheter, introducer and hemostasis valve of FIG. 1 being inserted into tissue;

FIG. 4 is a perspective view of the catheter and hemostasis valve after having been inserted into the tissue with the introducer being retracted therefrom;

FIG. 5 perspectively illustrates the manual removal of the hemostasis valve from the catheter, the latter being embedded within the tissue; and FIG. 6 is a side view of the hemostasis valve of the present invention, the first and second jaw portions thereof assuming a first inwardly biased configuration, and phantom portion representing a second configuration whereby the first and second jaw portions are separated from one another.

DETAILED DESCRIPTION OF THE PREFERRED EMBODIMENT

The detailed description set forth below in connection with the appended drawings is intended merely as a description of the presently preferred embodiment of the invention, and is not intended to represent the only form in which the present invention may be constructed or utilized. The description sets forth the functions and sequence of steps for construction and implementation of the invention in connection with the illustrated embodiments. It is to be understood, however, that the same or equivalent functions and sequences may be accomplished by different embodiment that are also intended to be encompassed within the spirit and scope of the invention.

Referring now to the figures, and initially to FIG. 1, there is shown a hemostasis valve 10 constructed in accordance with the preferred embodiment of the present invention. The valve 10 is specifically designed and configured to selectively maintain the lumen of a catheter in a closed state. However, as will be recognized, the valve 10, due to its novel and relatively simple construction, may be easily and readily utilized as a general utility clamp for use in a variety of applications.

As is well-known in the medical profession, catheters are typically intravenously inserted by means of an introducer 28 having the catheter assembly mounted thereon, the latter of which preferably comprises a conventional catheter 32 and catheter hub 34, the latter preferably comprising a convention lure-lock hub design. The catheter is typically carried upon the length of a medical needle 30 having a sharpened or beveled distal end and an opposing proximal end. When positioned upon the length of the needle 30, the catheter hub 34 is registered by engagement with the catheter hub mount 36 formed on the introducer 28. When so oriented, only the tip of the medical needle 30 extends beyond the end of the catheter 32 to allow insertion of the needle 30 and catheter 32 into a patient. As illustrated, the valve 10 is specifically designed and configured to be affixed upon a portion of the catheter 32 as the catheter 32, when interconnected with the introducer 28, is inserted into a patient, as discussed more fully below.

As more clearly seen in FIG. 2, the valve 10 generally comprises a single piece of wire 12 having opposed ends 12a, 12b, that is formed to have a first elongate jaw portion 14 defining a front end 16 and a back end 18, and a second elongate jaw portion 20 also defining a front end 22 and back end 24. Each opposed end 12a, 12b is preferably formed to define first and second arms 54, 56 that transversely extend across each respective jaw 14, 20 intermediate the respective front ends and back ends thereof. Specifically, first arm 54 extends transversely across first jaw portion 14 intermediate the front end 16 and back end 18 thereof while second arm 56 extends transversely across second jaw portion 20 intermediate the front end 22 and back end 24 thereof.

Extending between and interconnecting the first and second jaw portions 14, 20 and intermediate the front ends 16, 22 and back ends 18, 24 thereof is a spring portion 26. In the preferred embodiment, the spring portion 26 is sandwiched between first and second arms 54, 56 and is formed to have an arcuate configuration that bows outwardly toward the back ends 18, 24 of the first and second jaw portions 14, 20.

As further seen in FIG. 2, the first and second jaw portions are oriented on the opposed ends of the spring portion 26 in a manner wherein the front ends 16, 22 and back ends 18, 24 thereof are disposed in juxtaposed relation. As can additionally be seen in FIG. 2, first arm 54 and second arm 56 are in contact with spring portion 26 with first end 12a in contact with the vertical leg 18a of back end 18 and second end 12b being maintained in contact with the vertical leg 24a of back end 24.

As shown in FIG. 6, the spring portion 26 is operable to normally bias the front ends 16, 22 of the first and second jaw portions 14, 20 toward and preferably into abutting contact with each other. In this respect, the selective compression of the back ends 18, 24 of the first and second jaw portions 14, 20 toward each other in the directions C and D is operable to overcome the biasing force exerted by the spring portion 26 and cause the front ends 16, 22 to separate from each other in the directions E and F as shown in phantom in FIG. 6. To facilitate the user's ability to selectively compress the back ends such back ends 18, 24 are preferably formed to have a generally square-like shape to further enhance the gripping ability thereof when a compressive force is to be applied thereto, as seen in FIG. 5.

Additionally, as can be seen in FIG. 6, first arm 54 and second arm 56 are generally in line with or below the arcuate apex of spring portion 26 and are generally perpendicular relative axis AA. As a result of such contact between first arm 54 and second arm 56 with spring portion 26, two fulcrums 60, 62 are created to facilitate the separation of the front ends 16 and 22. As should be recognized, first arm 54 and second arm 56 are preferably formed below the centerline of the apex of spring portion 26. Otherwise, the separation of front ends 16 and 22 would be adversely compromised as the ends would not separate to the appropriate degree nor would the planes of the jaw members 14, 20 remain parallel to provide the most effective compressive forces. Additionally, it will be appreciated that if first end 12a and second end 12b did not contact and extend beyond the centerlines of the vertical legs of back ends 18 and 24 respectively, the maintenance of the fulcrums 60, 62 could be compromised.

While in the preferred embodiment the valve 10 is fabricated from a unitary piece of wire 12 formed to provide the valve 10 with a desired amount of resiliency, it will be recognized that alternative resilient materials may also be utilized.

With respect to usage of the valve 10 of the present invention, such valve 10 is initially positioned upon the interconnected catheter 32 and introducer 28, as seen in FIG. 1. As discussed above, in using the valve 10, compression of the back ends 18, 24 overcomes the biasing force exerted by spring portion 26 such that the respective front ends 16, 22 are separated from one another, thus enabling the device to be attached to the interconnected catheter 32 and introducer 28 as shown. Thereafter, the back ends 18, 24 are released, thus allowing the front ends 16, 22 of jaw members 14, 20 to bias inwardly toward each other.

While maintained in such configuration, the catheter 32 and introducer 28 may be advanced into the tissue 44 of a patient, as shown in FIG. 3. In this regard, the catheter 32 and introducer 28 are axially pierced through the tissue 44 by advancing the interconnected apparatus in the direction indicated by the letter A. As shown, valve 10 will be positioned sufficiently toward the proximal end of the catheter 32 such that the same does not interfere with the ability of the introducer 28 and catheter 32 to be sufficiently embedded within the tissue 44, as is necessary to establish sufficient intravenous penetration.

Thereafter, as illustrated in FIG. 4, once the catheter 32 and catheter hub 34 with valve 10 affixed thereto is sufficiently embedded within the tissue 44, the introducer 28, and more particularly needle 30 thereof, may be withdrawn proximally from the interior of the catheter 32. Advantageously, the valve 10, by virtue of the clamping effect produced by front ends 16, 22, causes the lumen of the catheter 32 to be maintained in a closed state, which thus prevents blood from flowing back therethrough.

When it becomes necessary to introduce fluids and/or medicines intravenously, a conventional fluid line 46 may be attached to the catheter hub 34, as shown in FIG. 5, and the valve 10 removed therefrom to thus enable the fluid to pass through the catheter 32 and ultimately into the patient. To release such valve 10, the user, with the user's index finger 48 and thumb 50, need only compress back ends 18, 20 towards one another to thus cause a corresponding separation of front ends 16, 22 a sufficient distance so that the valve 10 may be removed from the catheter 32.

As will be recognized, the valve 10 may either be formed to be disposable for single use or sterilization for re-use. Should the valve 10 be formed from sterilizable materials, the valve 10, in subsequent uses, may be attached and reattached to a given catheter 32 in the aforementioned manner.

Additionally, as discussed above, because of its simple and novel construction, the device 10 of the present invention lends itself to a variety of everyday applications. For example, the device 10 of the present invention may be utilized as a paper clip or, if appropriately dimensioned, as a clothespin or snack food bag clip.

Furthermore, although the invention has been described herein with specific reference to a presently preferred embodiment thereof, it will be appreciated by those skilled in the art that various additions, modifications, deletions and alterations may be made to such preferred embodiment without departing from the spirit and scope of the invention. Accordingly, it is intended that all reasonably foreseeable additions, modifications, deletions and alterations be included within the scope of the invention as defined in the following claims.

What is claimed is:

1. A clamping device, comprising:
    an elongate first jaw portion which defines front and back ends and extends along a longitudinal axis;
    an elongate second jaw portion which defines front and back ends and extends along the longitudinal axis;
    a first arm which is connected to the first jaw portion and extends in generally perpendicular relation to the longitudinal axis;
    a second arm which is connected to the second jaw portion and extends in generally perpendicular relation to the longitudinal axis; and
    an arcuate spring portion which defines an apex and is connected to the first and second jaw portions in a manner wherein the spring portion extends between the first and second arms and the apex of the spring portion is disposed between the first and second arms and the back ends of the first and second jaw portions;
    wherein the spring portion normally exerts a biasing force against the firs and second jaw portions which maintains the front ends thereof in contact which each other, with the application of compressive pressure to the back ends of the first and second jaw portions putting the spring portion into torsion and resulting in contact between the first and second arms and the spring portion at a pair of fulcrums disposed between the apex and the front ends which causes the compressive pressure applied to the back ends to overcome the biasing force exerted by the spring portion thus facilitating the separation of the front ends from each other.

2. The clamping device of claim 1 wherein the apex of the spring portion defines a centerline which extends in generally perpendicular relation to the longitudinal axis and in generally parallel relation to the first and second arms.

3. The clamping device of claim 1 wherein the clamping device is formed from an elongate piece of wire which is bent to form the first and second jaw portions, the first and second arms, and the spring portion.

4. The clamping device of claim 3 wherein the wire is bent such that the front ends of the first and second jaw portions are each formed to define a tapered distal end.

5. The clamping device of claim 3 wherein the wire is bent such that:
    the back ends of the first and second jaw portions are each formed to include a spaced pair of vertical legs; and
    the first and second arms are each formed to extend from one of the vertical legs of a respective one of the back ends to and into contact with the remaining vertical leg thereof.

* * * * *